United States Patent
Tabibian

(10) Patent No.: US 9,950,023 B1
(45) Date of Patent: Apr. 24, 2018

(54) COMPOSITION FOR THE TREATMENT OF ACNE

(71) Applicant: Parham Tabibian, MD, Inc., Los Angeles, CA (US)

(72) Inventor: Parham Michael Tabibian, Los Angeles, CA (US)

(*) Notice: Subject to any disclaimer, the term of this patent is extended or adjusted under 35 U.S.C. 154(b) by 597 days.

(21) Appl. No.: 14/550,108

(22) Filed: Nov. 21, 2014

(51) Int. Cl.
| | | |
|---|---|---|
| *A61K 36/00* | (2006.01) | |
| *A61K 36/41* | (2006.01) | |
| *A61K 31/198* | (2006.01) | |
| *A61K 31/455* | (2006.01) | |
| *A61K 31/05* | (2006.01) | |
| *A61K 31/353* | (2006.01) | |
| *A61K 31/07* | (2006.01) | |
| *A61K 31/593* | (2006.01) | |
| *A61K 31/355* | (2006.01) | |
| *A61K 31/105* | (2006.01) | |
| *A61K 35/644* | (2015.01) | |
| *A61K 36/88* | (2006.01) | |
| *A61K 31/4525* | (2006.01) | |

(52) U.S. Cl.
CPC .............. *A61K 36/41* (2013.01); *A61K 31/05* (2013.01); *A61K 31/07* (2013.01); *A61K 31/105* (2013.01); *A61K 31/198* (2013.01); *A61K 31/353* (2013.01); *A61K 31/355* (2013.01); *A61K 31/455* (2013.01); *A61K 31/4525* (2013.01); *A61K 31/593* (2013.01); *A61K 35/644* (2013.01); *A61K 36/88* (2013.01)

(58) Field of Classification Search
None
See application file for complete search history.

(56) References Cited

U.S. PATENT DOCUMENTS

2008/0292607 A1* 11/2008 Mazzio .................. A61K 31/19
424/94.1

OTHER PUBLICATIONS

Jacob et al, Neuroprotective effect of Rhodiola rosea Linn against MPTP induced cognitive impairment and oxidative stress. Annals of Neurosciences (2013), 20(2), 47-51.*
Shrivastava, Anti-apoptotic and anti-inflammatory effect of Piperine on 6-OHDA induced Parkinson's rat model. The Journal of nutritional biochemistry, (Apr. 2013) vol. 24, No. 4, pp. 680-687.*

* cited by examiner

*Primary Examiner* — Qiuwen Mi
(74) *Attorney, Agent, or Firm* — Michael D. Eisenberg

(57) ABSTRACT

An all-natural composition for treating acne, the composition comprising: N-acetylcysteine (NAC); Nicotinamide; Resveratrol; Rhodionin; Epigallocatechin gallate (EGCG); Vitamin A; Vitamin E; Vitamin D3, Allicin; and Propolis.

6 Claims, 1 Drawing Sheet

| |
|---|
| N-Acetylcysteine (NAC) |
| Nicotinamide |
| Resveratrol |
| Rhodiola |
| Epigallocatechin gallate (EGCG) |
| Vitamin A |
| Vitamin D3 |
| Vitamin E |
| Allicin |
| Propolis |

COMPOSITION FOR THE TREATMENT OF ACNE

TECHNICAL FIELD

The present invention, in some embodiments thereof, relates to the field of dermatology, and more particularly to the treatment of acne.

BACKGROUND OF THE INVENTION

Acne vulgaris (or simply acne) is a common human skin disease, characterized by presence of comedones (blackheads and whiteheads), papules (small pinkish 5 mm or smaller bumps), pustules (pus filled papules), nodules (large painful lesions located in the deeper portions of the skin), and in more severe forms, cystic abscess-like fluctuant lesions. Papules, pustules, nodules, and cystic type lesions, can all lead to secondary scarring. Severe inflammatory can manifest clinically by presence of not only comedones, but also by papules, pustules, nodules, and cystic lesions (with the cystic lesions representing the most severe manifestation of acne). Alternatively, in milder cases, acne can manifest clinically in non-inflammatory lesions such as open and closed comedones. It is important to realize, however, that even comedones have microscopically and histologically been shown to be accompanied by varying degrees of inflammation.

Acne more often affects skin with a greater numbers of oil glands; these areas include the face, the upper part of the chest, and the back. In adolescence, acne is usually caused by an increase in androgens such as testosterone, which occurs during puberty, regardless of sex. The psychosocial impact of acne has been well documented. Body image issues associated with acne can result in depression, anxiety, social isolation, low self-esteem, and even suicide.

Many different treatments have been proposed for decreasing acne. Some treatments involve dietary changes, such as eating fewer simple carbohydrates like sugar. Medications for acne include: benzoyl peroxide, antibiotics (either topical or by pill), retinoids (topical or oral) as with Isotretinoin (more commonly known as Accutane®), sulfur based medications, anti-androgen medications, hormonal treatments such as birth control pills, and alpha and beta hydroxyl acids (salicylic acid). Early and aggressive treatment is advocated by some to lessen the overall long-term impact to individuals.

The pathogenesis of acne, considered primarily to be a disease of the pilosebaceous unit, is attributed to multiple factors such as increased sebum production, alterations of the quality of sebum lipids, inflammatory processes, dysregulation of the hormone microenvironment, and interaction with neuropeptides, follicular hyperkeratinization and the proliferation of pathogenic bacteria within the follicle. In particular, the sebaceous gland plays an important role in the initiation of the disease, as this gland possesses all the enzyme machinery for the production of hormones and cytokines.

The pathogenic bacteria involved in acne is the *Propionibacterium acnes* (*P. acnes*), a gram positive anaerobic bacteria that grows deep inside of pores, where it feeds on the sebum that is produced by the sebaceous glands that surround the base of the hair shaft. *P. acnes* bacteria use sebum, which is produced in follicles, as a primary source of food. *P. acnes* bacteria use specialized enzymes that digest the fatty acids and triglycerides that are abundant in sebum. In an anaerobic environment, *P. acnes* ferments the fatty acids and triglycerides, and releases short chain fatty acids and propionic acid as metabolic byproducts (hence, the name *Propionibacterium*). The cellular damage, metabolic byproducts and bacterial debris produced by the rapid growth of *P. acnes* in follicles can trigger secondary inflammation, which is a contributing factor to the severity of acne symptoms.

Among the factors implicated in acne occurrence, sebum secretion can be considered as the major one. Increased sebum secretion is a characteristic of acne patients. Along with the increased sebum secretion, several qualitative modifications have been described in acne patients, underlying the pivotal role played by lipid mediators derived from sebum alterations in acne pathogenesis. Human sebum contains triglycerides, wax esters, squalene, cholesterol esters, cholesterol, and free fatty acids. Triglycerides and fatty acids, taken together, account for the predominant proportion (about 57.5%), followed by wax esters (about 26%) and squalene (about 12%). Abnormal activity of specific desaturase enzymes and/or excessive sebum secretion can result in an alteration of the relative proportion of the different fatty acids, and leading to compositional changes that can initiate and exacerbate acne symptoms. This accounts for modifications in the amount, and type of fatty acids which have been observed in acne patients. Specifically and importantly squalene peroxide, a by-product of lipid peroxidation derived from sebum, has been recognized to play a crucial role in the development of inflammatory reactions as well as in cytotoxicity and comedogenesis.

BRIEF SUMMARY OF EMBODIMENTS OF THE INVENTION

Many treatments known in the prior art involve introduction into the patient's body of artificial compositions which, while being beneficial for acne treatment, may have unwanted side effects. For example, antibiotic treatment may give rise to bacterial resistance to antibiotics. Other side effects caused by commonly used acne treating artificial (antibiotic and non-antibiotic) compositions may include candidal overgrowth, skin rashes including photosensitivity, and gastrointestinal side effects such as nausea, vomiting, and diarrhea. The introduction of the compositions into the patient's body may be via application of medication to the skin, or via oral ingestion.

Classically, the most recognized pathogenic mechanisms of acne include: (I) Abnormal keratinization, (II) excessive sebum buildup, (III) *P. acnes* bacterium, and (IV) ensuing inflammatory response. These mechanisms are generally decreased (i.e. treated) in the known compositions for treating acne.

Inflammation is regarded as a key component of the pathogenesis of acne. In the last few years, there has been a debate as to whether hyperkeratinization of the follicular duct precedes the influx of inflammatory cells or vice versa. Recent studies support the notion that in influx of inflammatory cells and cytokines such as IL-1 occurs before the hyperproliferation around uninvolved follicles and this triggers the activation of the keratinocytes leading to hyperkeratinization of the follicular epithelium. Thus, inflammation appears to both precede the initial lesion of acne (comedone), and is certainly an important last step of acne pathogenesis, manifesting clinically as papules, pustules, and nodules/abscesses which can result in acne scarring.

From a clinical point of view, some of the common causative clinical factors in acne include: (V) the role of hormones, i.e. androgens, and (VI) stress, as reported by many, if not most, acne patients. Clinical and experimental evidence indicates that androgens affect sebaceous gland function. When free testosterone enters the cell, the testosterone is quickly reduced to 5α-dihydrosterone (DHT) by the 5α-reductase enzyme. DHT increases sebaceous gland size by increasing sebocyte proliferation and the rate of total lipid synthesis. Androgens exert their effect on sebaceous glands by increasing the proliferation of sebocytes and increasing lipid production.

In addition to the above mechanisms, the inventor has found that (VII) the role of biofilms is much lesser discussed and/or known pathogenic factor in acne, and is therefore not commonly addressed by known treatments.

While bacteria have classically been viewed from the perspective of planktonic, free floating pathogens proliferating and exerting their virulence as individual organisms, it is now recognized that microbes also can exist as multicellular consortiums known as biofilms. A biofilm is any group of microorganisms in which cells stick to each other on a surface. These first colonists adhere to the surface initially through weak, reversible adhesion forces called van der Waals forces. If the colonists are not immediately separated from the surface, they can anchor themselves more permanently using cell adhesion structures such as pili. The biofilm itself is held together and protected by a matrix of secreted polymeric compounds called EPS (extracellular polymeric substance or exopolysaccharide). The EPS is composed of polysaccharides, proteins, lipids, and extracellular DNA (eDNA) and is considered to be the hallmark of biofilm formation. In addition to facilitating attachment, the EPS also serves a protective function by preventing neutrophilic penetration, masking phagocytic detection of opsonins, and sequestering host antibodies.

Biofilm formation is an important aspect of many, if not most bacterial diseases, such as valve endocarditis, osteomyelitis, and dental caries. Established biofilms can tolerate antimicrobial agents at concentrations of 10-1000-times larger than the concentrations needed to kill genetically equivalent planktonic bacteria. Biofilms are also extraordinarily resistant to phagocytosis, making biofilms extremely difficult to eradicate from living hosts.

The inventor has found that nearly all current literature points to the presence of biofilms as being the cause of bacterial resistance to all antibiotics, and hence the reason and explanation for more prolonged treatments with topical and/or oral antibiotics. As such, the dosage and/or composition of antibiotics are changed to overcome antibiotic resistance. Importantly, with respect to acne, the inhibition and/or damaging of established biofilms, as a direct and specific strategy to treat acne, is not directly addressed in current acne treatments.

Because of the extended length of treatment necessary for acne to respond to oral antibiotics (which are generally more efficiently absorbed by the human body than their topical counterparts), the inventor has found that biofilms play a direct pathogenic role in acne. That is, in addition to increasing antibiotic resistance, the formation of biofilms is a direct cause for the development of acne. In fact, the development of *Propionibacterium acnes* (*P. acnes*) within the pilosebaceous unit may be dependent on the creation of biofilm. *P. acnes* live as a community of bacteria that encase themselves within an extracellular polysaccharide substance (gylcocalyx polymer), which the organisms secrete after adherence to the surface. This gylcocalyx polymer acts as a protective exoskeleton and serves as a physical barrier, limiting effective antimicrobial concentrations within the biofilm microenvironment. As such, the development of a biofilm with its protective exoskeleton creates bacterial colonies that are increasingly resistant to antibiotic treatments.

Further evidence for the presence of biofilms in acne is predominantly derived from the ability of *P. acnes* to form biofilms both in vitro and on implanted medical devices. The formation and behavior of the entire biofilm community is directed by signaling molecules that are produced when microorganisms reach a critical number. This phenomenon is termed quorum sensing (QS) and has also been shown to regulate the expression of virulence factors as well as modulate host immunity. Lastly, sequencing of the *P. acnes* genome reveals the presence of genes involved in the production of EPS and QS molecules. Moreover, keratin plugging has long been considered a key component of acne pathogenesis; the adhesive properties of the EPS produced by *P. acnes* biofilms in sebum may be responsible for the tenacious binding of keratinocytes to the infundibular epithelium. Thus, in contrast with the prior art which seeks to circumvent biofilm formation by changing dosages and compositions of antibiotics, the inventor has found that it would beneficial to directly address the formation of biofilms in order to treat acne.

An in vitro study evaluating multiple anti-acne agents alone or in combination found that only 0.1% triclosan, 5% benzoyl peroxide+0.5% erythromycin, and 5% benzoyl peroxide+1% clindamycin were effective in both reducing biofilm mass and killing >99% of biofilm-associated *P. acnes*. These compounds, however, are known to be associated with side effects. Studies have indicated that exposure to triclosan may increase the incidence of hay fever, food allergies, and allergic contact dermatitis. The carcinogenic potential of benzoyl peroxide has been highlighted by some studies. Erythromycin may cause bacterial resistance to antibiotics and may have adverse effects when used concomitantly with other drugs. Clindamycin may cause bacterial resistance to antibiotics. Furthermore adverse effects of topical application of clindamycin may include dryness, burning, itching, scaliness, or peeling of skin, erythema, and oiliness.

Collectively, the above mentioned pathogentic and clinical factors, along with the much less discussed and recognized role of biofilms have never been addressed by a single known composition for treating acne. There is therefore a need to have a single composition to help treat a plurality of above pathogenic factors of acne. There is also a need for a natural composition, which is less likely to cause side effects generally found in artificial compositions.

The present invention aims at providing a natural composition which addresses a plurality of pathogenic and clinical factors of acne. The composition of the present invention is configured for being orally introduced into the patient's body.

The present invention relates to a composition for treating acne. The composition comprising: N-Acetylcysteine (NAC); Nicotinamide; Resveratrol; *Rhodiola*; Epigallocatechin gallate (EGCG); Vitamin A; Vitamin D3; Vitamin E; Allicin; and Propolis.

In a variant, the composition includes: about 200-1200 mg of NAC; about 50-500 mg of *Aloe barberdensis*; about 100-500 mg of Nicotinamide; about 100-1000 mg of Resveratrol; about 100-500 mg of *Rhodiola*; about 100-500 mg of EGCG; about 10000-400000 IU of Vitamin A; about 400-5000 IU of Vitamin D3; about 300-800 IU of Vitamin E; and 100-300 mg of Propolis.

In another variant, Allicin is in a form of garlic oil concentrate and/or stabilized allicin complex.

Optionally, the composition includes a quantity of allicin equivalent to an amount of allicin present in about 1-10 mg of garlic oil concentrate or in 25-500 mg of stabilized allicin complex.

Optionally, the composition includes a quantity of allicin equivalent to an amount of allicin present in about 1 mg of garlic oil concentrate or in about 50 mg of stabilized allicin complex.

In a variant, the composition comprises about 1 mg of garlic oil concentrate.

In another variant, the composition comprises about 50 mg of stabilized allicin complex.

In yet another variant, the composition comprises a mixture of garlic oil concentrate and stabilized allicin complex, the mixture comprising a quantity of allicin equivalent to an amount of allicin present in about 1 mg of garlic oil concentrate or in about 50 mg of stabilized allicin complex.

In some embodiments of the present invention, the composition includes *Aloe barberdensis*.

In a variant, the composition comprises about 50-500 mg of *Aloe barberdensis*.

In some embodiments of the present invention, the composition includes: about 200 mg of Nicotinamide; about 200 mg of NAC; about 100 mg of Resveratrol; about 100 mg of *Rhodiola*; about 100 mg of EGCG; about 25000 IU of Vitamin A; about 2000 IU of Vitamin D3; about 400 IU of Vitamin E; and about 100 mg of Propolis.

In a variant, the composition includes about 50 mg of *Aloe barberdensis*.

In another variant, the composition further comprises piperine.

In yet another variant, the composition further comprises about 2.5-15 mg of piperine.

In a further variant, the composition further comprises about 4 mg of piperine.

According to another aspect of some embodiments of the present invention, the present invention relates to a pill or capsule configured for being ingested, containing the above composition.

According to another aspect of some embodiments of the present invention, the present invention relates to a method for treating acne, comprising orally administering the above composition.

According to another aspect of some embodiments of the present invention, the present invention relates to a method for treating acne, comprising orally administering the above composition each day.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 1 is a block diagram of an embodiment in accordance with the principles of the invention.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

An aspect of some embodiments of the present invention relates to a natural composition for acne treatment configured to for oral intake.

The composition of the present invention includes: Allicin (present as garlic oil extract and/or stabilized allicin complex in the composition), propolis, N-Acetylcysteine, Resveratrol, Nicotinamide, Rhodionin, Epigallocatechin gallate (EGCG), Vitamin A, Vitamin D3, and Vitamin E. Optionally, the composition further includes *Aloe barberdensis* (aka: *aloe vera*).

The inventor has found that stabilized Allicin (or garlic oil concentrate containing Allicin) is effective in attacking/penetrating biofilms. Allicin is the primary active ingredient in garlic. However, in its native form, allicin is considered to be highly volatile and transient. Allicin is produced as a result of the interaction of the enzyme alliinase with garlic's alliin when garlic is damaged (e.g.) chopped or crushed. In the human body, allicin activates genes which in turn cause release and activation of internal enzymatic antioxidant defenses (such as glutathione, catalase, and superoxide dismutase), which in turn are responsible for its health-promoting effects in the human body. For optimal delivery, Allicin must either be properly stabilized, be procured from sources that have already properly stabilized allicin, or be supplied from garlic oil concentrates. In order to provide allicin, the composition of the present invention may include garlic oil concentrate and/or stabilized allicin complex. In some embodiments of the present invention, the composition of the present invention includes a quantity of allicin present in about 1-10 mg of garlic oil concentrate, which corresponds to about 25-500 mg of stabilized allicin complex. In a non-limiting example, the composition of the present invention includes a quantity of allicin present in about 1 mg of garlic oil concentrate, which corresponds to about 50 mg of stabilized allicin complex. For example, the composition of the present invention may include about 1 mg of garlic oil, or about 50 mg of stabilized allicin complex. Alternatively, the composition of the present invention includes a mixture of garlic oil and of stabilized allicin complex, such that the quantity of allicin included in the composition is equivalent to the quantity if allicin in 1 mg of garlic oil concentrate, or in about 50 mg of stabilized allicin complex. For example, to reach the desired quantity of allicin, the mixture may include 0.5 mg of garlic oil concentrate and 25 mg of stabilized allicin complex, or 0.25 mg of garlic oil concentrate and 37.5 mg of stabilized allicin complex, or 0.75 mg of garlic oil concentrate and 12.5 mg of stabilized allicin complex.

Propolis is produced by bees as a natural resin to build their hives. Initially gathered from the leaf buds of trees and certain vegetable, the bee gathers and transforms Propolis in order to disinfect the beehive, seal cracks, build panels, as well as using it as a microbiocidal agent and disinfectant. As such, propolis is directly responsible for creating a nearly aseptic environment inside the beehives, protecting them from viruses and bacteria. Well known and documented beneficial properties of propolis are its antioxidant, anti-inflammatory, and anti-microbial actions. For example, propolis has shown efficacy against herpes simplex virus types 1 and 2 and parasitic infections in several studies. However, and importantly for this present composition, propolis has been included for its role against biofilms. Previously, ethanolic extracts of propolis have demonstrated reduction of biofilm formation ability, and the intensity of proliferation against the *S. epidermidis* bacteria. As such, propolis is included in the present composition for the expected efficacy of propolis against the propniobacterium acnes, which is a gram positive anaerobic bacterium as is the *S. epidermidis*. In a non-limiting example, the composition of the present invention includes 100-300 mg of propolis, for example, about 100 mg of propolis.

N-Acetylcysteine (NAC) is made from the amino acid cysteine joined to an acetyl group. This addition of an acetyl group makes NAC a more potent antioxidant than the amino acid cysteine. This nutrient is a strong antioxidant. NAC donates the amino acid cysteine to help form the antioxidant glutathione, a powerful natural antioxidant normally found in the body. NAC is included in the composition of the present invention for its inhibitory effects against biofilms produced by various bacteria such as Staph epidermidis and *Enterococcus faecalis*. The biofilm inhibitory properties of NAC are hereby being incorporated in the current composition against the *P. acnes* bacteria. In a non-limiting example, the composition of the present invention includes about 200-1200 mg, for example, about 200 mg.

Resveratrol (aka: trans-resveratrol) is a key active component of *Polygonum cuspidatum* extracts. Resveratrol is commonly known for its anti-inflammatory and antioxidant effects. However, Resveratrol's anti-androgen and biofilm inhibitory properties are much less commonly recognized and discussed. Moreover, clinical tests have shown that trans Resveratrol extracts can inhibit *P. acnes* biofilm formation by 99.2%. The quantity of Resveratrol in the composition of the present invention may be 100-1000 mg, for example about 100 mg.

*Aloe vera* (*aloe barberdensis*) contains 75 potentially active constituents. These include vitamins, enzymes, minerals, sugars, lignin, saponins, salicylic acids and amino acids. With respect to vitamins, it contains vitamins A (beta-carotene), C and E, which are antioxidants. With respect to enzymes, it contains 8 enzymes: aliiase, alkaline phosphatase, amylase, bradykinase, carboxypeptidase, catalase, cellulase, lipase, and peroxidase. The combination of its antioxidants and enzymatic components is responsible for the overall anti-inflammatory property of *Aloe vera*. The composition of the present invention may include 50-500 mg of *aloe barberdensis*, for example, about 50 mg.

Nicotinamide (aka Niacinamide, Vitamin B3) is configured for decreasing sebum production (by inhibiting sebaceous lipogenesis) and providing an anti-inflammatory effect. Nicotinamide has been shown to be an effective treatment for skin inflammation in various conditions, including acne vulgaris by decreasing interleukin-8 (IL-8) production in a dose-dependent manner. *Propionibacterium acnes* (*P. acnes*) has been shown to activate interleukin-8 (IL-8) secretion by interacting with Toll-like receptor 2 (TLR-2) on the surface of keratinocytes. The quantity of nicotinamide in the composition of the present invention may be 100-2000 mg, for example, about 100 mg.

*Rhodiola* (aka: *Rhodiola Rosea*) is an adaptogen, plant-based compound that promotes homeostasis. Specifically, *rhodiola* has protective properties that include reduction of stress-induced cortisol levels. The quantity of *rhodiola rosea* in the composition of the present invention may be 100-500 mg, for example, about 100 mg.

Epigallocatechin gallate (EGCG) is configured for reducing sebum production, and having anti-inflammatory benefits. The quantity of EGCG in the composition of the present invention may be 100-500 mg, for example about 100 mg.

Vitamin A, a retinoid, is configured for normalizing keratinization and reducing sebum production. This nutrient, which is stored in the liver, is found also in the skin, particularly in the sebaceous glands which have been shown to contain express retinoid receptors. The susceptibility of keratinocytes to the anti-proliferative effects of vitamins A and D has been reported. The quantity of Vitamin A in the composition of the present invention may be 10,000-400000 International Units (IU), for example about 10,000 IU.

Vitamin D3 suppresses cell proliferation in the sebaceous glands, prevents the enlargement of the sebaceous glands, and reduces the production of sebum. Vitamin D3 also produces an antimicrobial effect through a group of natural antibacterial agents called cathelicidins. The quantity of Vitamin D3 in the composition of the present invention may be 400-5000 IU, for example about 2000 IU.

Vitamin E has a beneficial role in lipid peroxidation in sebaceous glands as explained below. Increasing amounts of data seem to confirm the presence of alterations in sebum from acne patients. Altered ratio between saturated and unsaturated fatty acids has been indicated as an important feature to be considered in addition to the altered amount of specific fatty acids such as linoleic acid. Furthermore, particular attention has been focused on squalene peroxide that seems to be able to induce an inflammatory response beyond cytotoxicity and comedones formation. In addition to inciting an inflammatory response, squalene peroxide has also been demonstrated to be comedogenic. A positive correlation was found between degree of squalene peroxidation and size of the comedones elicited. In addition, marked hyperplasia and hyperkeratosis of the epithelium in follicular infundibulum and marked proliferation of sebaceous glands were observed. The strategy that skin adopts to limit the potentially harmful effects of peroxidated squalene relies on the vitamin E supply to the skin surface. Vitamin E is delivered directly onto the skin via the activity of the sebaceous gland. Consequently, Vitamin E is considered to be the major sebum antioxidant. The quantity of Vitamin E in the composition of the present invention may be 300-800 IU, for example, about 400 IU.

Optionally, the composition of the present invention includes piperine. Piperine, which is an ingredient derived from black pepper, is known to enhance the overall absorption of the other ingredients that piperine is ingested with. In some embodiments of the present invention, 4 mg of piperine are included in the present composition, to enhance absorption of the composition. In a variant, 2.5-15 mg of piperine is included in to the composition of the present invention.

The composition of the present invention comprehensively and uniquely addresses the presence and proliferation of *P. acnes* biofilms, abnormal keratinization, excessive sebum buildup, significant inflammatory response, role of hormones, and stress-induced cortisol in the initiation and exacerbation of acne. No other acne formulation addresses the plurality of factors (both physiological and clinical) addressed by the current composition. Furthermore, no other oral formulation has addressed the significant role of biofilms as the current composition. By addressing a wide range of factors which contribute to the development of acne, the composition of the present invention can be used to effectively treat acne. The following table summarizes the factors that are treated by each of the above-mentioned components of the composition of the present invention.

composition, and less resultant inflammation. Thus the dosages of ingredients addressing the role of sebaceous glands and ingredients addressing the inflammatory component are reduced.

Furthermore, it should be noted that all the compounds listed above are either natural or directly derived from natural sources (such as NAC) and do not contain antibiotics. In fact, allicin is an organosulfur compound obtained from garlic. Propolis is a resinous mixture that honey bees collect from tree buds, sap flows, or other botanical sources. NAC is a combination of the amino acid cysteine and an acetyl group. Cysteine is present in most high protein foods. When NAC is ingested, the body converts NAC to cysteine, which is then converted to glutathione, an antioxidant.

*Aloe* powder is extracted from the *aloe vera* plant. Nicotinamide occurs in trace amounts mainly in meat, fish, nuts, and mushrooms, as well as to a lesser extent in some vegetables. Vitamin D3 is naturally (but in a limited amount) manufactured by the body from sunlight (UVB). Vitamin E is found in such foods as seeds, nuts, and green leafy vegetables.

Resveratrol is a phenolic compound that has been found to have a strong antioxidant activity, with trans-resveratrol being the active form of the resveratrol polyphenol. Resveratrol is typically found in the skin, seeds, and stems of grapes. Plants create resveratrol to protect themselves against the stress caused by things such as poor growing conditions, severe weather conditions, and when under attack by pathogens such as bacteria or fungi. Resveratrol's

| Factors addressed: | Biofilm | Keratinization | Stress/Cortisol | Androgens | Excessive Sebum buildup | Altered sebum composition | Inflammation |
|---|---|---|---|---|---|---|---|
| 1. Allicin | +++ | | | | | | |
| 2. Propolis | +++ | | | | | | +++ |
| 3. EGCG | | | | | +++ | | +++ |
| 4. Niacinamide | | | | | +++ | | +++ |
| 5. NAC | +++ | | | | | | +++ |
| 6. Rhodiola | | | +++ | | | | |
| 7. Vitamin A | | +++ | | | +++ | | |
| 8. Resveratrol | +++ | | | +++ | | | +++ |
| 9. ALOE | | | | | | | +++ |
| 10. Vitamin D3 | | ++++ | | | +++ | | +++ |
| 11. Vitamin E | | | | | | +++++ | ++++ |

In contrast with the prior art, the composition of the present invention, has a comprehensive effect on the etiologic factors listed above, which include both clinically aggravating elements (hormones and stress) as well as physiologic elements (with significant emphasis on the far less discussed and recognized role of biofilms in acne). Furthermore, the chosen ingredients have both overlapping as well as complementary beneficial attributes which work in concert and thus synergistically together to address the specific etiologic factors listed. It is this synergistic combination of ingredients that has enabled the inventor to incorporate dosages of individual compositions that are lower than what would be expected to be clinically efficacious than when administered individually.

The synergy among the different ingredients forming the present composition also occurs when multiple factors that play a role in a condition such as acne are all addressed simultaneously. Thus, for example, if the level of excess androgens has been suppressed by a first group of ingredients, the result is less sebum buildup, thus less altered sebum anti-inflammatory properties are due to its inhibition of pro-inflammatory cytokines, Cox-1 and Cox-2.

*Rhodiola rosea* (aka: arctic or golden root) is one of only 16 scientifically established adaptogenic plant. It is a perennial flowering plant in the family Crassulaceae. Vitamin A can be found in the form of retinol in animal food sources, while carotenes which are used for the production of vitamin A in the human body, can be found in many fruits and vegetables. ECGC is found mainly in white tea, green tea and, in smaller quantities, black tea.

The composition of the present invention can be used by itself or as a supplement to other treatments. The composition of the present invention is optionally packaged in a capsule and is configured for being ingested. The quantities of the compounds of the composition of the present invention are examples of quantities that may beneficial to acne prevention/elimination if taken during a period of about 24 hours. Different patients may respond to these compounds in different manners. Therefore, the scope of the present invention extends to any composition having different quantities of the above compounds.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A composition for treating acne, the composition comprising an effective amount of:
   about 200-1200 mg of NAC;
   about 100-500 mg of Nicotinamide;
   about 100-1000 mg of Resveratrol;
   about 100-500 mg of *Rhodiola*;
   about 100-500 mg of EGCG;
   about 10000-400000 IU of Vitamin A;
   about 400-5000 IU of Vitamin D3;
   about 300-800 IU of Vitamin E;
   Allicin; and
   100-300 mg of Propolis.

2. The composition of claim 1, comprising about 50-500 mg of *Aloe barberdensis*.

3. A composition for treating acne, the composition comprising an effective amount of:
   N-Acetylcysteine (NAC),
   Nicotinamide,
   Resveratrol,
   *Rhodiola*,
   Epigallocatechin gallate (EGCG),
   Vitamin A,
   Vitamin D3,
   Vitamin E,
   Allicin; and
   Propolis,
   wherein Allicin is in a form of garlic oil concentrate and/or stabilized allicin complex; and wherein the allicin is in a quantity equivalent to an amount of allicin present in about 1-10 mg of garlic oil concentrate in 25-500 mg of stabilized allicin complex.

4. The composition of claim 3, comprising a mixture of garlic oil concentrate and stabilized allicin complex, the mixture comprising a quantity of allicin equivalent to an amount of allicin present in about 1 mg of garlic oil concentrate or in about 50 mg of stabilized allicin complex.

5. A composition for treating acne, the composition comprising an effective amount of:
- about 200 mg of Nicotinamide;
- about 200 mg of NAC;
- about 100 mg of Resveratrol;
- about 100 mg of *Rhodiola*;
- about 100 mg of EGCG;
- about 25000 IU of Vitamin A;
- about 2000 IU of Vitamin D3;
- about 400 IU of Vitamin E;
- about 100 mg of Propolis; and allicin.

6. The composition of claim 5, comprising about 50 mg of *Aloe barberdensis*.

* * * * *